United States Patent
Iannotti et al.

(10) Patent No.: US 10,605,785 B2
(45) Date of Patent: Mar. 31, 2020

(54) SENSOR SYSTEM AND METHOD

(71) Applicant: General Electric Company, Schenectady, NY (US)

(72) Inventors: Joseph Iannotti, Glenville, NY (US); Christopher James Kapusta, Delanson, NY (US); David Richard Esler, Gloversville, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 134 days.

(21) Appl. No.: 15/616,105

(22) Filed: Jun. 7, 2017

(65) Prior Publication Data

US 2018/0356368 A1  Dec. 13, 2018

(51) Int. Cl.

| | | |
|---|---|---|
| *G01N 29/22* | (2006.01) | |
| *G01K 11/26* | (2006.01) | |
| *B23K 1/002* | (2006.01) | |
| *G01L 1/16* | (2006.01) | |
| *G01L 3/00* | (2006.01) | |
| *G01N 29/24* | (2006.01) | |
| *G01L 19/14* | (2006.01) | |

(52) U.S. Cl.
CPC .......... *G01N 29/223* (2013.01); *B23K 1/002* (2013.01); *G01K 11/265* (2013.01); *G01L 1/165* (2013.01); *G01L 3/00* (2013.01); *G01L 19/147* (2013.01); *G01N 29/2462* (2013.01)

(58) Field of Classification Search
CPC .... G01N 29/223; G01N 29/041; G01N 29/14; G01N 29/2462; G01N 29/2475; G01N 29/2481; G01K 11/265; G01L 1/165; G01L 3/00

USPC ....... 73/660, 659, 587, 588, 593; 310/313 R, 310/313 B, 328
See application file for complete search history.

(56) References Cited

U.S. PATENT DOCUMENTS

| | | | |
|---|---|---|---|
| 5,102,029 A | * | 4/1992 | Richardson ............. H01L 23/66 228/124.1 |
| 5,459,368 A | | 10/1995 | Onishi et al. |
| 6,853,067 B1 | | 2/2005 | Cohn et al. |

(Continued)

FOREIGN PATENT DOCUMENTS

| | | |
|---|---|---|
| CN | 102175358 A | 9/2011 |
| CN | 103924204 B | 12/2015 |

(Continued)

OTHER PUBLICATIONS

Feiertag et al., "Surface acoustic wave component packaging", ResearchGate, Jan. 2007.

(Continued)

*Primary Examiner* — Suman K Nath
(74) *Attorney, Agent, or Firm* — Philip S. Hof; The Small Patent Law Group LLP (57) ABSTRACT

A system includes a structure configured to have a structure bonding layer disposed on a surface of the structure. The structure bonding layer is a metallic alloy. The system includes a sensor configured to have a sensor bonding layer disposed on a surface of the sensor. The sensor bonding layer is a metallic alloy. The sensor bonding layer is configured to be coupled to the structure bonding layer via a metallic joint in order for the sensor to sense data of the structure through the metallic joint, the structure bonding layer, and the sensor bonding layer.

18 Claims, 3 Drawing Sheets

(56) References Cited

U.S. PATENT DOCUMENTS

| | | |
|---|---|---|
| 7,239,068 B2 | 7/2007 | Miyaji |
| 7,605,466 B2 | 10/2009 | Aimi et al. |
| 9,543,736 B1 | 1/2017 | Barwicz et al. |
| 2007/0046142 A1 | 3/2007 | Obara et al. |
| 2007/0105341 A1 | 5/2007 | Sosnowchik et al. |
| 2007/0188054 A1 | 8/2007 | Hasken et al. |
| 2010/0132404 A1* | 6/2010 | Shuja ............... F25B 39/02 62/524 |
| 2012/0078313 A1* | 3/2012 | Hasse ............... A61F 2/442 606/305 |
| 2013/0044322 A1* | 2/2013 | Feitisch ........... H01S 5/02272 356/432 |
| 2015/0185247 A1 | 7/2015 | Eid et al. |
| 2015/0264808 A1* | 9/2015 | Bretschneider ...... H05K 1/0212 174/262 |
| 2015/0373964 A1* | 12/2015 | Gaag ............... A01L 1/00 59/61 |
| 2016/0181202 A1* | 6/2016 | Gong ............... H01L 23/5389 257/762 |
| 2016/0268190 A1* | 9/2016 | McKnight-MacNeil ............... H01L 23/49562 |
| 2016/0282204 A1* | 9/2016 | Haines ............... G01L 1/165 |
| 2017/0063326 A1 | 3/2017 | Kapusta et al. |

FOREIGN PATENT DOCUMENTS

| | | |
|---|---|---|
| DE | 198 56 951 A1 | 10/1999 |
| WO | 2001067058 A1 | 9/2001 |

OTHER PUBLICATIONS

"NanoFoil", Indium Corporation, http://www.indium.com/nanofoil/, Retrieved on Mar. 22, 2017.

Extended European Search Report and Opinion issued in connection with corresponding EP Application No. 18175715.4 dated Nov. 15, 2018.

* cited by examiner

SENSOR SYSTEM AND METHOD

FIELD

The subject matter described herein relates to sensors.

BACKGROUND

Sensors may be used in a variety of applications. For example, in electro-mechanical systems, surface acoustic wave (SAW) devices may be used as sensors to measure torque, temperature, pressure, and other parameters. The SAW devices may be wafer level hermetically capped or placed and sealed inside of hermetic discrete packages, and then mounted onto structures in order to sense data of the structure. The SAW devices may be mounted onto structures such as shafts, rods, blades, or alternative structures used in various applications such as aviation, oil and gas, transportation, renewable energy extraction, or the like.

The processes of mounting sensors to structures presently include several issues. One issue present with mounting sensors to certain structures is that many structures are too large to fit into conventional ovens or reflow equipment or may not be able to be transported to a location having conventional ovens or reflow equipment to mount the sensors to the structure. Therefore, many SAW devices are mounted to structures using an adhesive or epoxy material. However, using an epoxy or adhesive to mount a sensor to a structure limits the operating temperature of the system, reduces the sensitivity of the sensor to sense data of the structure, limits the capability of future re-workability of the sensors mounted to the structures, and requires significant time for the epoxy or adhesive to properly cure, which increases associated manufacturing and material costs. It is advantageous to have a more robust mounting method to attach these sensors both in the field and in a production setting.

BRIEF DESCRIPTION

In one embodiment, a system includes a structure configured to have a structure bonding layer disposed on a surface of the structure. The structure bonding layer is a metallic alloy. The system includes a sensor configured to have a sensor bonding layer disposed on a surface of the sensor. The sensor bonding layer is a metallic alloy. The sensor bonding layer is configured to be coupled to the structure bonding layer via a metallic joint in order for the sensor to sense data of the structure through the metallic joint, the structure bonding layer, and the sensor bonding layer.

In one embodiment, a method includes disposing a structure bonding layer on a surface of a structure. The structure bonding layer is a metallic alloy. The method includes disposing a sensor bonding layer on a surface of a sensor. The sensor bonding layer is a metallic alloy. The structure bonding layer is coupled to the sensor bonding layer via a metallic joint in order for the sensor to sense data of the structure through the metallic joint, the structure bonding layer, and the sensor bonding layer.

In one embodiment, a system includes a structure configured to have a structure bonding layer disposed on a surface of the structure. The structure bonding layer is a metallic alloy. The system includes a sensor configured to have a sensor bonding layer disposed on a surface of the sensor. The sensor bonding layer is a metallic alloy. The sensor bonding layer is configured to be coupled to the structure bonding layer via a metallic joint at a location outside of a reflow oven in order for the sensor to sense data of the structure through the metallic joint, the structure bonding layer, and the sensor bonding layer.

BRIEF DESCRIPTION OF THE DRAWINGS

The inventive subject matter will be better understood from reading the following description of non-limiting embodiments, with reference to the attached drawings, wherein below.

DETAILED DESCRIPTION

One or more embodiments of the inventive subject matter described herein provide for systems and methods having a sensor that is disposed on a structure via a metallic sensor bonding layer and a metallic structure bonding layer joined to a metallic joint in order to sense data of the structure through the metallic joint, the sensor bonding layer, and the structure bonding layer. The structures may be a large structure such as rods, shafts, blades, or the like, used in applications such as aviation, oil and gas, transportation, renewable energy extraction, power and energy systems, or the like. The sensor may sense temperature data, strain data, stress data, or the like or combinations thereof, of the structure. For example, the sensor may sense temperature data of a conduit that transfers oil, may sense the temperature of the oil that is transferred inside of the conduit, may sense the strain of a rotating shaft, or the like. The systems and methods described herein improves sensor sensitivity, enables exposure of systems to higher operating temperatures, and reduces an amount of creep of the bonding materials relative to systems that do not have a metallic bond.

Figure 1:
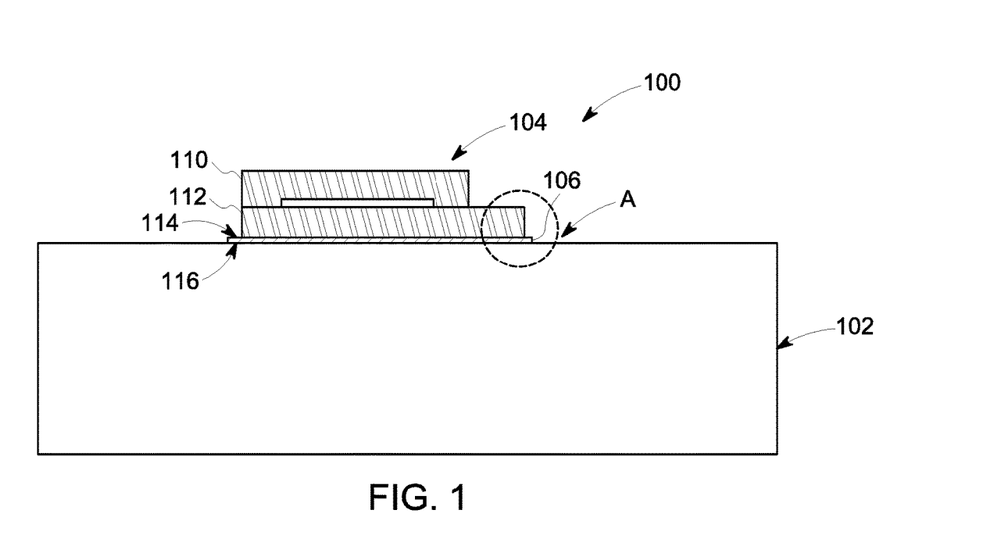
FIG. 1 illustrates a cross-sectional view of a system in accordance with one embodiment.

FIG. 1 illustrates a cross-sectional view of a system 100 in accordance with one embodiment. The system 100 includes a sensor 104 that is coupled to a structure 102. The structure 102 may be a shaft, a plate, a blade, a rod, or the like. The structure 102 may be a manufactured out of a metallic and/or non-metallic material. For example, the structure 102 may be a steel shaft used to transfer oil or gas, may be an aluminum rotor blade of a wind turbine, may be a steel rotating or stationary shaft of an aerial device, or the like. Optionally, the structure 102 may be any alternative component used in applications such as aviation, oil and gas, transportation, renewable energy extraction, power and energy systems, or the like.

The sensor 104 has a first component 110 that is bonded to a second component 112. The first and second components 110, 112 of the sensor 104 may be single crystal quartz wafers that are coupled together by a liquid crystal polymer (LCP) material. Optionally, the sensor 104 may have more than two or less than two components. Optionally, the components of the sensor 104 may be held together by any alternative material. The sensor 104 may be a SAW device, or any alternative sensor that is used to sense data. For example, the sensor 104 may be a SAW device that includes a strain gauge, torque sensor, temperature sensor, or the like, that is used to sense temperature data, strain data, stress data, or the like, of the structure 102. Optionally, the sensor 104 may be any alternative sensor that senses (e.g., records, collects, reads, measures, or the like) information about the structure 102.

The sensor 104 is coupled to a first side 114 of a metallic joint 106 of the system 100. Additionally, the structure 102 is coupled to an opposite, second side 116 of the metallic joint 106. The sensor 104 is operably coupled to the structure 102 via the metallic joint 106 in order to sense data of the structure. In the illustrated embodiment of FIG. 1, a surface of the sensor 104 that is coupled to the first side 114 of the metallic joint 106 and a surface of the structure 102 that is coupled to the second side 116 of the metallic joint 106 are planar or substantially planar surfaces (within manufacturing tolerances). Optionally, one or more of the sensor 104 or the structure 102 may have non-planar surfaces that are coupled to the metallic joint 106. For example, the structure 102 may be a shaft that has a cross-sectional shape that is generally circular and the sensor 104 is operably coupled to the circular cross-sectional shape of the outer surface of the shaft structure 102. Optionally, the structure 102 may be a blade with a curved outer surface and the sensor 104 is operably coupled to the curved outer surface of the blade structure 102.

In one embodiment, the system 100 includes a structure 102 having multiple sensors 104 that are operably coupled with the structure 102 via a metallic joint 106. For example, the multiple sensors 104 may be arranged as an array of multiple sensors 104 in columns and rows or may be randomly arranged and coupled with one or more surfaces of the structure 102. Optionally, the system 100 may have one or more metallic joints 106 that couple the sensors 104 with the structure 102. For example, a single metallic joint 106 may couple multiple sensors 104 with the structure 102, multiple metallic joints 106 may couple the multiple sensors 104 with the structure 102, or the like.

Figure 2:
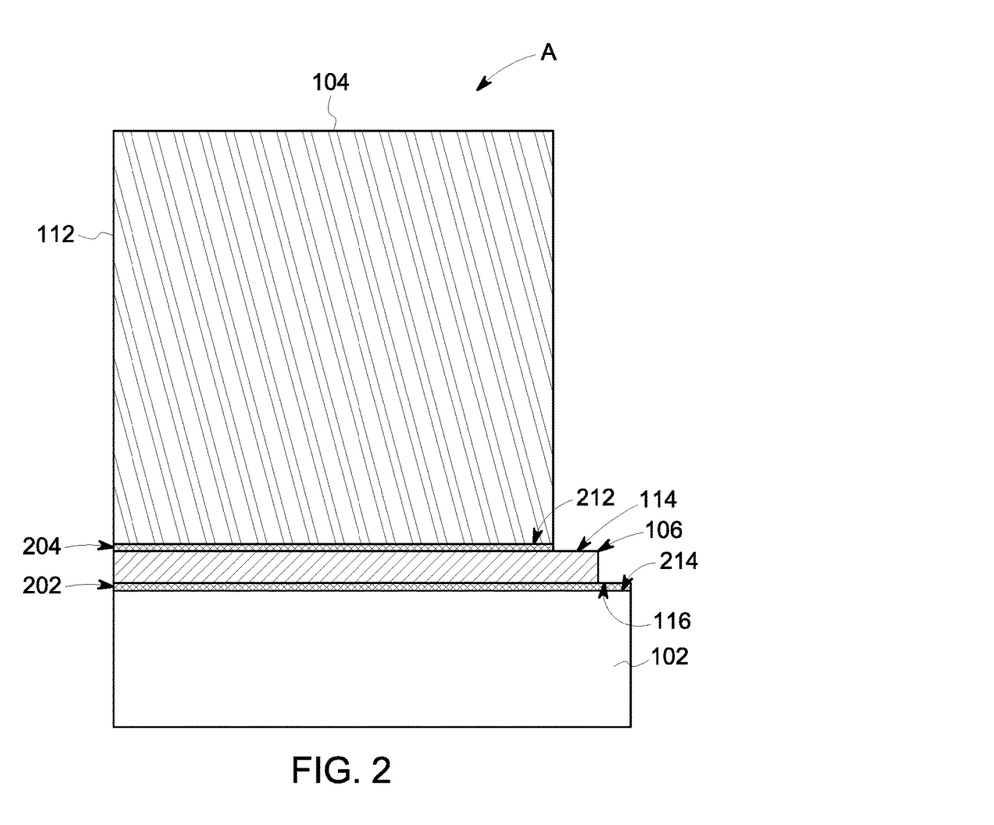
FIG. 2 illustrates a partial cross-sectional view of the system of FIG. 1 in accordance with one embodiment.

FIG. 2 illustrates a partial cross-sectional view A of the system 100 of FIG. 1 including the sensor 104 that is made of a quartz/non-metallic material in accordance with one embodiment. The sensor 104 has a sensor bonding layer 204 that is disposed on a surface 212 of the sensor 104. The sensor bonding layer 204 is a metallic alloy that can be coupled to the metallic joint 106. For example, the sensor bonding layer 204 may be a layer of titanium, copper, silver, tin, nickel, gold, electroless nickel immersion gold (eNIG), or the like, that is disposed on the surface 212 of the sensor 104. Optionally, the sensor bonding layer 204 may be any metallic compound and/or metal alloy that may be bonded to the metallic joint 106 and that provides adhesion between the sensor 104 and the structure 102. The sensor bonding layer 204 may be a metallic alloy that has a higher operating temperature and a higher modulus of elasticity relative to an epoxy, adhesive, liquid crystal polymer, or the like. Additionally or alternatively, the sensor 104 may be manufactured of a metallic material. For example, the system 100 may be devoid of the sensor bonding layer 204 and the metallic sensor 104 may be coupled to the metallic joint 106.

The structure 102 has a structure bonding layer 202 that is disposed on a surface 214 of the structure 102. In one embodiment, the surface 214 may be an outer, or exterior surface of the structure 102 that is metallic and allows for metallic bonding between the structure and the metallic joint 106. Optionally, the surface 214 may be an interior surface of a structure 102. For example, the sensor 104 may be bonded to the interior of the structure 102 (e.g., the interior of a hollow shaft, or the like) and the structure bonding layer 202 may be disposed on an interior surface 214 of the structure 102.

The structure bonding layer 202 is a metallic alloy that can be coupled to the metallic joint 106. For example, the structure bonding layer 202 may be electroless nickel immersion gold (eNIG), electrolytic nickel gold (NiAu), or the like, when there cannot be a direct metallic bond between a non-metallic structure 102 and the sensor 104, or when the structure 102 and/or the sensor 104 are made of materials that are not applicable for metallic bonding and/or wetting. Optionally, the structure bonding layer 202 may be any metallic compound and/or metallic alloy that may be bonded to the metallic joint 106. In one or more embodiments, the structure bonding layer 202 may be a local metallization of the surface 214 of the structure 102. For example, the structure 102 may be manufactured out of a material that may be able to be soldered to the second side 116 of the metallic joint 106 (e.g., the structure 102 may be manufactured out of a steel alloy). Optionally, the structure bonding layer 202 may be a layer of a material suitable for metallic bonding that is disposed on the surface 214 of the structure 102. For example, the structure 102 may be manufactured out of a material that may not be able to be soldered to the second side 116 of the metallic joint 106 (e.g., the structure 102 may be manufactured out of a brass alloy, a non-steel alloy, or the like). The structure bonding layer 202 may be a metallic alloy that has a higher operating temperature and a higher modulus of elasticity relative to an epoxy, adhesive, liquid crystal polymer, or the like.

The metallic joint 106 is a metallic bond that operably couples the sensor 104 with the structure 102. Non-limiting examples of the material of the metallic joint 106 include solder alloys (by percent weight) 96.5% tin-3% silver-0.5% copper; 80% gold-20% tin; 92.5% lead-5% tin-2.5% silver; 88% gold-12% germanium; or 82% gold-18% indium. Optionally, the metallic joint 106 may be any alternative materials and/or alloys. Non-limiting examples may include transient liquid phase sintering, sintered silver, sintered copper, sintered nickel, braze alloys, or the like.

The sensor bonding layer 204 is coupled to the first side 114 of the metallic joint 106, and the structure bonding layer 202 is coupled to the second side 116 of the metallic joint 106 in order to operably couple the sensor 104 with the structure 102. The sensor 104 senses data of the structure 102 through the metallic joint 106, the sensor bonding layer 204 and the structure bonding layer 202. The sensor 104 may sense temperature, strain, stress, pressure, or the like, of the structure 102. For example, a torque may be applied to the structure 102. The sensor 104 may measure the stress or strain on the structure 102 that is transferred through the structure bonding layer 202, the metallic joint 106, and the sensor bonding layer 204 to the sensor 104.

In one embodiment, the modulus of elasticity of the material of the sensor bonding layer 204 and the modulus of elasticity of the material of the structure bonding layer 202 impacts the amount of strain data that is transferred from the structure 102 through the structure bonding layer 202, the metallic joint 106, and the sensor bonding layer 204 to the sensor 104. For example, as the modulus of elasticity of the material of the sensor and structure bonding layers 204, 202 increases (e.g., the materials become more stiff), the accuracy of the sensor 104 measuring strain data of the structure increases. Alternatively, as the modulus of elasticity of the material of the sensor and structure bonding layers 204, 202 decreases (e.g., the materials become less stiff), the accuracy of the sensor 104 measuring strain data of the structure decreases. For example, the sensor 104 that is operably coupled with the structure 102 via the metallic joint 106 is more accurate relative to the sensor 104 that is operably coupled with the structure 102 via an adhesive and/or epoxy material. Additionally, the sensor 104 that is operably coupled with the structure 102 via the metallic joint 106 may be used in systems having higher operating temperatures relative to the sensor 104 that is operably coupled with the structure 102 via an adhesive and/or epoxy material. Additionally, the sensor 104 that is operably coupled with the structure 102 via the metallic joint 106 may have less creep of the metallic joint than the sensor 104 that is operably coupled with the structure 102 via an adhesive and/or epoxy. To achieve acceptable strain transfer from the structure 102 to the sensor 104, the modulus of elasticity in the bonding layers 204, 202 may have a minimum value of 700 MPa. In order to increase accuracy of the strain data that is transferred to the sensor 104, it is advantageous to have a modulus of elasticity include and above 2000 MPa. Additionally, the modulus of elasticity at varying temperatures may impact the accuracy of the strain data that is transferred to the sensor 104. Non-limiting metals, metal alloys, and/or metallic materials disclosed have sufficient modulus of elasticity at high temperatures. For example, in conventional epoxy materials, the modulus decreases at temperatures greater than 150° C. Alternatively, metals and/or metal alloys can be used between 40% to 75% of the homologous temperature with minimal creep. In the alloys listed, the homologous temperature may have a temperature greater than 1000° C.

Figure 3:
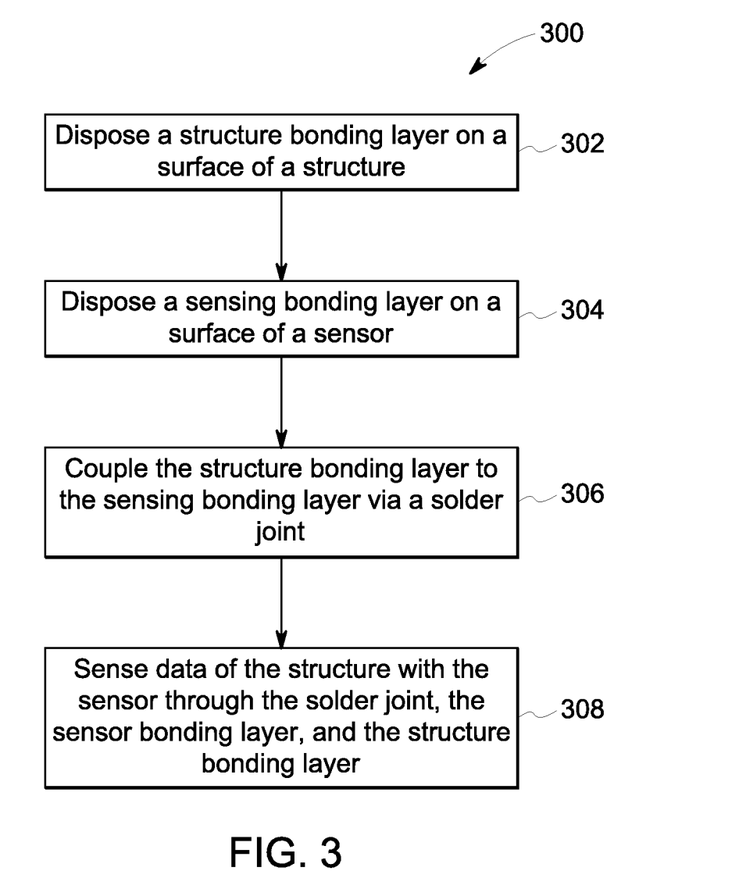
FIG. 3 illustrates a method flowchart in accordance with one embodiment.

FIG. 3 illustrates a method flowchart 300 of the system 100 in accordance with one embodiment. At 302, a structure bonding layer 202 is disposed on a surface 214 of a structure 102. For example, the structure bonding layer 202 may be a local metallization of the surface 214 of the structure 102, or the structure bonding layer 202 may be a layer of a solderable material that is disposed on the surface 214 of the structure 102. The structure bonding layer 202 may have a surface area on the surface 214 of the structure 102 that is substantially equivalent to a surface area of the surface 212 of the sensor 104. Optionally, the structure bonding layer 202 may have a surface area that is greater than or less than the surface area of the surface 212 of the sensor 104. Optionally, the structure bonding layer 202 may have a surface area that is substantially the same as the surface area of the metallic joint 106, may have a surface area that is less than the surface area of the metallic joint 106, or may have a surface area that is greater than the surface area of the metallic joint 106.

At 304, a sensor bonding layer 204 is disposed on a surface 212 of a sensor 104. For example, the sensor bonding layer 204 may be a layer of a metallic material. The structure bonding layer 202 and the sensor bonding layer 204 may be a common or unique metallic alloys. The sensor bonding layer 204 may have a surface area that is substantially equivalent to a surface area of the surface 212 of the sensor 104, may have a surface area that is less than the surface area of the surface 212, or may have a surface area that is greater than the surface area of the surface 212. Optionally, the sensor bonding layer 204 may extend an area that is substantially equivalent to, is less then, or is greater than the surface area of the metallic joint 106.

In one or more embodiments, the sensor bonding layer 204 and/or the structure bonding layer 202 use self-orientation or self-alignment to assemble the sensor 104 to the structure 102 via the metallic joint 106. The metallic joint 106 may be a solder layer made of a solder alloy having wetting properties that enables the sensor bonding layer 204 of the sensor 104 to self-align with the structure bonding layer 202 of the structure 102 when the sensor 104 is bonded to the structure 102. For example, the metallic joint 106 allows the sensor 104 to self-align with the structure 102 without the use of additional pick-and-place equipment, additional fixture equipment, or the like.

At 306, the structure bonding layer 202 is coupled to the sensor bonding layer 204 via the metallic joint 106. For example, the sensor bonding layer 204 is coupled with a first side 114 of the metallic joint 106, and the structure bonding layer 202 is coupled with an opposite, second side 116 of the metallic joint 106.

The sensor 104 is operably coupled with the structure 102 via the metallic joint 106 at a location outside of a conventional reflow oven. For example, the structure 102 may be part of an assembly that may not be able to be transferred to a reflow oven, the structure 102 may not be able to be disassembled from the assembly to be transferred to a reflow oven, the structure 102 may not be able to fit inside of a reflow oven, the structure 102 may be manufacture out of a material that cannot withstand conventional operating temperatures of a conventional reflow oven, or the like.

Figure 4:
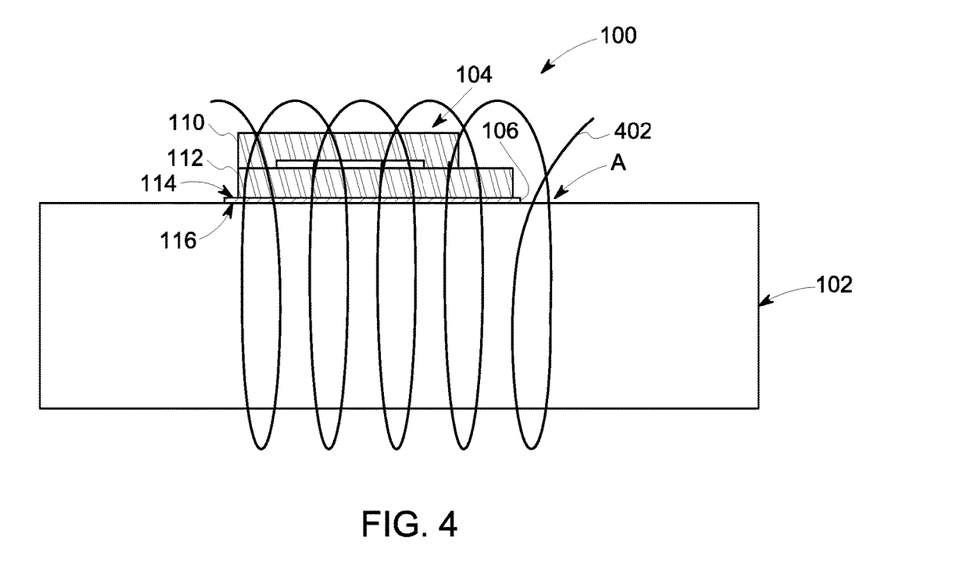
FIG. 4 illustrates a cross-sectional view of a system in accordance with one embodiment.

In one embodiment illustrated in FIG. 4, the sensor 104 is operably coupled with the structure 102 via the metallic joint 106 by an induction coil 402 that applies electrical stimuli to the metallic joint 106. For example, the sensor 104 may be held in a position (e.g., by a fixture, by an operator, or the like) and the induction coil 402 may be placed in contact with, close by to, around, or the like, the sensor 104 and the substrate 102 to which the sensor 104 is to be bonded to. In one embodiment, the induction coil 402 may be wrapped around the system 100, as illustrated in FIG. 4. Additionally or alternatively, the induction coil 402 may be wrapped around the sensor 104 such that the induction coil 402 is substantially parallel to the substrate 102. Additionally or alternatively, the induction coil 402 may be placed in contact with the system 100 by an alternative configuration. The induction coil 402 applies localized electrical stimuli to the metallic joint 106 to activate reflow the metallic joint 106 in order to operably couple the sensor 104 with the structure 102.

Figure 5:
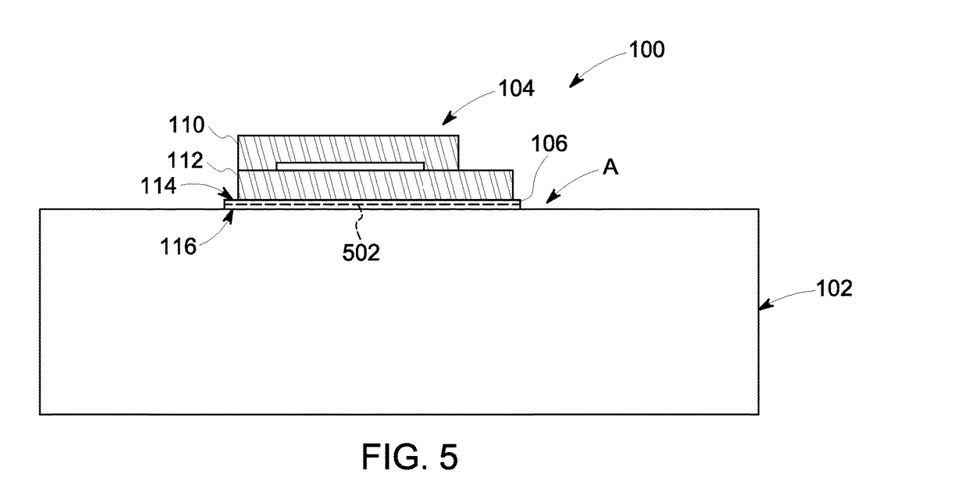
FIG. 5 illustrates a cross-sectional view of a system in accordance with one embodiment.

In one embodiment illustrated in FIG. 5, the sensor 104 is operably coupled with the structure 102 via the metallic joint 106 by an active reflow process at the metallic joint 106. For example, an exothermic metallic film such as a Reactive Nano Technologies (RNT) film 502, or an alternative material, may be placed within the metallic joint 106 in order to locally reflow the metallic joint 106. The sensor 104 may be held in a position (e.g., by a fixture, by an operator, or the like). Electrical stimuli that is applied to the film 502 by a fixture, an electrical source, or the like, activates reflow of the metallic joint 106 in order to operably couple the sensor 104 with the structure 102.

Returning to FIG. 3, at 308, the sensor 104 senses data of the structure 102 through the structure bonding layer 202, the metallic joint 106, and the sensor bonding layer 204. For example, the sensor 104 may sense (e.g., collect, read, measure, obtain, or the like) data of the structure 102. The sensed data of the structure 102 transfers from the structure 102, through the metallic joint 106, through the metallic structure bonding layer and sensor bonding layer, to the sensor 104. For example, as the modulus of elasticity of the metallic sensor bonding layer 204 and the structure bonding layer 202 increases, the transfer of the sensed strain data of the structure 102 improves relative to a non-metallic sensor bonding layer 204 and non-metallic structure bonding layer 202. The data of the structure 102 may include temperature, pressure, stress, strain, or the like. Optionally, the data of the structure 102 may include sensed data of a fluid that is being contained inside of the structure 102. Optionally, the data of the structure 102 may include sensed data of an externality characteristic to which the structure 102 is exposed (e.g., environmental ambient temperature, ambient pressure, ambient humidity, or the like). Optionally, the sensed data of the structure 102 may include any alternative data that is sensed (e.g., collected, measured, read, obtained, or the like) by the sensor 104.

In one embodiment of the subject matter described herein, a system includes a structure configured to have a structure bonding layer disposed on a surface of the structure. The structure bonding layer is a metallic alloy. The system includes a sensor configured to have a sensor bonding layer disposed on a surface of the sensor. The sensor bonding layer is a metallic alloy. The sensor bonding layer is configured to be coupled to the structure bonding layer via a metallic joint in order for the sensor to sense data of the structure through the metallic joint, the structure bonding layer, and the sensor bonding layer.

Optionally, the sensor bonding layer is configured to be coupled to the structure bonding layer via the metallic joint at a location outside of a reflow over.

Optionally, the data of the structure includes one or more of temperature data, stress data, or strain data.

Optionally, the structure is one or more of a shaft, a rod, or a blade.

Optionally, the sensor is configured to self-align with the structure via the metallic joint.

Optionally, the structure bonding layer is configured to be disposed on an outer surface of the structure.

Optionally, the system includes an induction coil configured to be in operational contact with the metallic joint. The induction coil is configured to apply electrical stimuli to the metallic joint.

Optionally, the sensor is a surface acoustic wave (SAW) device.

Optionally, the SAW device comprises one or more of a strain gauge, a torque sensor, or a temperature sensor.

In one embodiment of the subject matter described herein, a method includes disposing a structure bonding layer on a surface of a structure. The structure bonding layer is a metallic alloy. The method includes disposing a sensor bonding layer on a surface of a sensor. The sensor bonding layer is a metallic alloy. The structure bonding layer is coupled to the sensor bonding layer via a metallic joint in order for the sensor to sense data of the structure through the metallic joint, the structure bonding layer, and the sensor bonding layer.

Optionally, coupling the sensor bonding layer to the structure bonding layer via the metallic joint occurs at a location that is outside of a reflow over.

Optionally, the data of the structure includes one or more of temperature data, stress data, or strain data.

Optionally, the structure is one or more of a shaft, a rod, or a blade.

Optionally, the sensor is configured to self-align with the structure via the metallic joint.

Optionally, the structure bonding layer is configured to be disposed on an outer surface of the structure.

Optionally, the method includes applying electrical stimuli to the metallic joint with an induction coil configured to be in operation contact with the metallic joint.

Optionally, the sensor is a surface acoustic wave (SAW) device.

Optionally, the SAW device comprises one or more of a strain gauge, a torque sensor, or a temperature sensor.

In one embodiment of the subject matter described herein, a system includes a structure configured to have a structure bonding layer disposed on a surface of the structure. The structure bonding layer is a metallic alloy. The system includes a sensor configured to have a sensor bonding layer disposed on a surface of the sensor. The sensor bonding layer is a metallic alloy. The sensor bonding layer is configured to be coupled to the structure bonding layer via a metallic joint at a location outside of a reflow oven in order for the sensor to sense data of the structure through the metallic joint, the structure bonding layer, and the sensor bonding layer.

Optionally, the sensor is a surface acoustic wave (SAW) device.

As used herein, an element or step recited in the singular and proceeded with the word "a" or "an" should be understood as not excluding plural of said elements or steps, unless such exclusion is explicitly stated. Furthermore, references to "one embodiment" of the presently described inventive subject matter are not intended to be interpreted as excluding the existence of additional embodiments that also incorporate the recited features. Moreover, unless explicitly stated to the contrary, embodiments "comprising," "including," or "having" (or like terms) an element, which has a particular property or a plurality of elements with a particular property, may include additional such elements that do not have the particular property.

As used herein, terms such as "system" or "controller" may include hardware and/or software that operate(s) to perform one or more functions. For example, a system or controller may include a computer processor or other logic-based device that performs operations based on instructions stored on a tangible and non-transitory computer readable storage medium, such as a computer memory. Alternatively, a system or controller may include a hard-wired device that performs operations based on hard-wired logic of the device. The systems and controllers shown in the figures may represent the hardware that operates based on software or hardwired instructions, the software that directs hardware to perform the operations, or a combination thereof.

As used herein, terms such as "operably connected," "operatively connected," "operably coupled," "operatively coupled" and the like indicate that two or more components are connected in a manner that enables or allows at least one of the components to carry out a designated function. For example, when two or more components are operably connected, one or more connections (electrical and/or wireless connections) may exist that allow the components to communicate with each other, that allow one component to control another component, that allow each component to control the other component, and/or that enable at least one of the components to operate in a designated manner.

It is to be understood that the subject matter described herein is not limited in its application to the details of construction and the arrangement of elements set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter, and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A system comprising: a structure configured to have a structure bonding layer disposed on a surface of the structure, wherein the structure bonding layer is a metallic alloy; and
   a sensor configured to have a sensor bonding layer disposed on a surface of the sensor, wherein the sensor bonding layer is a metallic alloy;
   wherein the sensor bonding layer is configured to be coupled to the structure bonding layer via a metallic joint in order for the sensor to sense data of the structure through the metallic joint, the structure bonding layer, and the sensor bonding layer,
   and wherein the metallic joint comprises 5% or more of tin;
   the sensor further comprising: a first component; and a second component coupled to the first component via a liquid crystal polymer (LCP) material, wherein the sensor is configured to self-align with the structure via the metallic joint, and wherein each of the first component and the second component comprise single crystal wafers.

2. The system of claim 1, wherein the sensor bonding layer is configured to be coupled to the structure bonding layer via the metallic joint at a location outside of a reflow oven, and wherein the metallic joint comprises about 96.5% tin, about 3% silver, and about 0.5% copper.

3. The system of claim 1, wherein the data of the structure includes one or more of temperature data, stress data, or strain data,
   and wherein the metallic joint comprises about 20% tin and about 80% gold.

4. The system of claim 1, wherein the structure is one or more of a shaft, a rod, or a blade, and wherein the metallic joint comprises about 92.5% lead, about 5% tin, and about 2.5% silver.

5. The system of claim 1, wherein the structure bonding layer is configured to be disposed on an outer surface of the structure, and wherein the sensor bonding layer comprises a higher modulus of elasticity than the liquid crystal polymer (LCP) material.

6. The system of claim 1, further comprising an induction coil configured to be in operational contact with the metallic joint, the induction coil configured to apply electrical stimuli to the metallic joint, wherein each of the sensor bonding layer and the structure bonding layer comprises a modulus of elasticity of at least about 700 MPa.

7. The system of claim 1, wherein the sensor is a surface acoustic wave (SAW) device, and wherein each of the sensor bonding layer and the structure bonding layer comprises a modulus of elasticity of at least about 2000 MPa.

8. The system of claim 7, wherein the SAW device comprises one or more of a strain gauge, a torque sensor, or a temperature sensor.

9. A method comprising:
   disposing a structure bonding layer on a surface of a structure, wherein the structure bonding layer is a metallic alloy;
   disposing a sensor bonding layer on a surface of a sensor, wherein the sensor bonding layer is a metallic alloy;
   coupling the structure bonding layer to the sensor bonding layer via a metallic joint in order for the sensor to sense data of the structure through the metallic joint, the structure bonding layer, and the sensor bonding layer,
   wherein the sensor is configured to self-align with the structure via the metallic joint,
   placing an exothermic metallic film within the metallic joint; and
   locally reflowing the metallic joint,
   wherein the structure bonding layer comprises at least one of electroless nickel immersion gold (eNIG) or electrolytic nickel gold (NiAu).

10. The method of claim 9, wherein coupling the sensor bonding layer to the structure bonding layer via the metallic joint occurs at a location that is outside of a reflow oven, and wherein the metallic joint is composed of at least 82% gold.

11. The method of claim 9, wherein the data of the structure includes one or more of temperature data, stress data, or strain data, and wherein the metallic joint comprises at least 12% of at least one of germanium or indium.

12. The method of claim 9, wherein the structure is one or more of a shaft, a rod, or a blade, wherein the metallic joint comprises at least one of: transient liquid phase sintering, sintered silver, sintered copper, sintered nickel, or a braze alloy.

13. The method of claim 9, wherein the structure bonding layer is configured to be disposed on an outer surface of the structure,
   and wherein the metallic joint comprises about 88% gold and about 12% germanium.

14. The method of claim 9, further comprising applying electrical stimuli to the metallic joint with an induction coil configured to be in operational contact with the metallic joint,
   wherein the metallic joint comprises about 82% gold and about 18% indium.

15. The method of claim 9, wherein the sensor is a surface acoustic wave (SAW) device.

16. The method of claim 15, wherein the SAW device comprises one or more of a strain gauge, a torque sensor, or a temperature sensor.

17. A system comprising:
   a structure configured to have a structure bonding layer disposed on a surface of the structure, wherein the structure bonding layer is a metallic alloy; and
   a sensor configured to have a sensor bonding layer disposed on a surface of the sensor, wherein the sensor bonding layer is a metallic alloy;
   wherein the sensor bonding layer is configured to be coupled to the structure bonding layer via a metallic joint at a location outside of a reflow oven in order for the sensor to sense data of the structure through the metallic joint, the structure bonding layer, and the sensor bonding layer,
   wherein the sensor bonding layer comprises at least one of tin or electroless nickel immersion gold (eNIG);
   wherein the sensor is configured to self-align with the structure via the metallic joint;
   an exothermic metallic film is placed within the metallic joint; and
   wherein the metallic joint is locally reflowed.

18. The system of claim 17, wherein the sensor is a surface acoustic wave (SAW) device.

* * * * *